(12) United States Patent
Levi

(10) Patent No.: US 10,206,763 B1
(45) Date of Patent: Feb. 19, 2019

(54) RESTORED ANTERIOR ENDODONTICALLY TREATED TEETH

(71) Applicant: Jack Levi, Teaneck, NJ (US)

(72) Inventor: Jack Levi, Teaneck, NJ (US)

( * ) Notice: Subject to any disclaimer, the term of this patent is extended or adjusted under 35 U.S.C. 154(b) by 0 days.

(21) Appl. No.: 14/569,912

(22) Filed: Dec. 15, 2014

Related U.S. Application Data

(63) Continuation-in-part of application No. 13/329,717, filed on Dec. 19, 2011.

(51) Int. Cl.
  *A61C 13/08* (2006.01)

(52) U.S. Cl.
  CPC .................. *A61C 13/082* (2013.01)

(58) Field of Classification Search
  CPC .. A61C 5/02; A61C 5/04; A61C 5/023; A61C 5/045; A61C 13/30
  USPC .................. 428/432; 433/220–224
  See application file for complete search history.

(56) References Cited

U.S. PATENT DOCUMENTS

| | | | | |
|---|---|---|---|---|
| 3,541,688 | A * | 11/1970 | Hughes et al. | 433/208 |
| 4,936,776 | A | 6/1990 | Kwiatkoski et al. | |
| 5,217,375 | A * | 6/1993 | Oden et al. | 433/218 |
| 6,132,215 | A | 10/2000 | Prasad et al. | 433/220 |
| 8,722,100 | B2 * | 5/2014 | Lovschall et al. | 424/602 |
| 2004/0038178 | A1 * | 2/2004 | Mayer et al. | 433/169 |
| 2005/0227203 | A1 * | 10/2005 | Kuperman | 433/218 |
| 2005/0227204 | A1 | 10/2005 | Hauck et al. | |
| 2009/0047635 | A1 * | 2/2009 | Behrend et al. | 433/225 |
| 2011/0212419 | A1 * | 9/2011 | Schweiger | 433/202.1 |
| 2013/0337412 | A1 * | 12/2013 | Kwon | 433/183 |

OTHER PUBLICATIONS

Influence of post placement in the fracture resistance of endodontically treated incisors veneered with direct composite, Baratieri et al., The journal of prosthetic dentistry, vol. 84, No. 2, Aug. 2000, pp. 180-184.*
Management of Transverse root fracture by dowel-inlay: A case report, Sunil Reddy, Journal of International Oral Health, Feb. 2011, vol. 3, issue 1.*
Adapting Fiber-Reinforced Composite root canal posts for use in noncircular-shaped cnals, Nicola Grande, Pract Prodecures Aesthetic Dentistry, 2006, 18(8): A-G.*

* cited by examiner

*Primary Examiner* — Yogesh P Patel
*Assistant Examiner* — Matthew P Saunders

(57) ABSTRACT

This invention is a method and product that can be restored with a porcelain facial veneer, ENDODONTIC VENEER EV™ made of hard porcelain material such as IPS EMAX™ or zirconia porcelain, as well as Ceram layering ceramic and other porcelain materials. The facial incisal and lingual surfaces of teeth are prepared minimally. A labial chamfer of 0.3-0.5 mm is prepared labially into enamel extending 1.5 mm to the incisal. A rhomboid access inlay preparation is made on the lingual surface with an extended post 3-5 mm below the height of the crest of bone, extending into a post space barrier cement 1.5 mm to form a secondary ferrule. The invention prevents bacterial microleakage to the apex and tooth fracture. It will also prevent root canal failures.

9 Claims, 5 Drawing Sheets

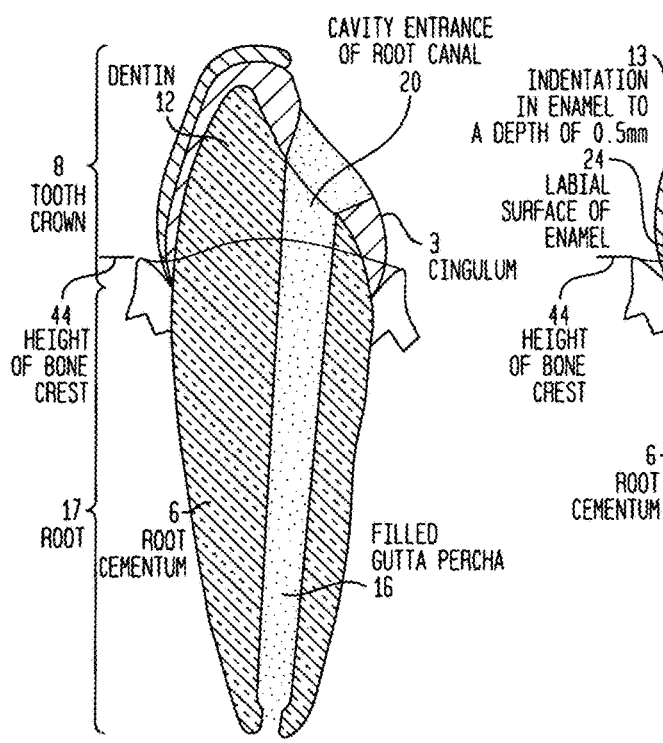
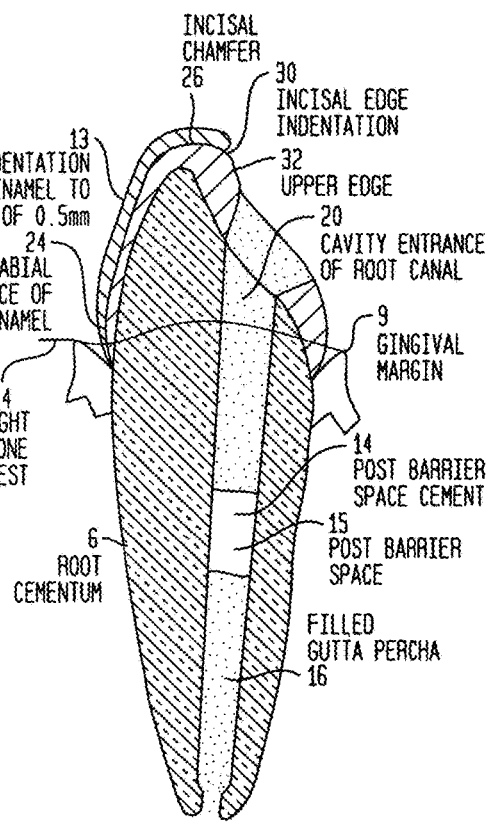

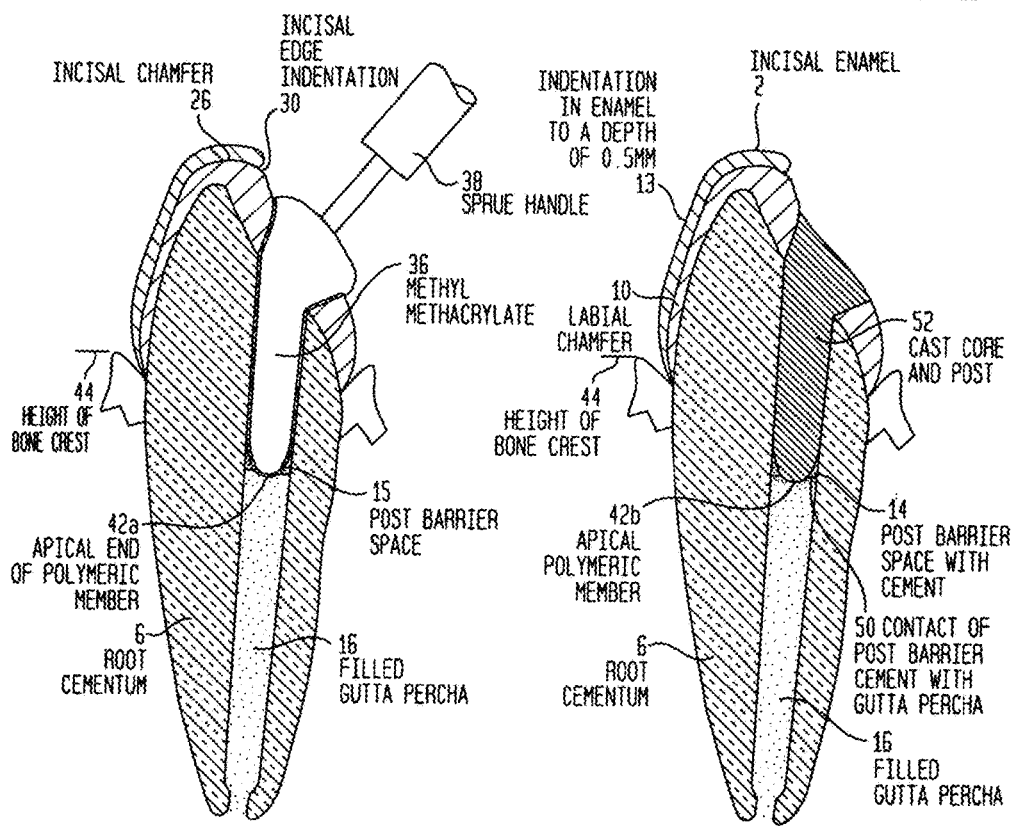

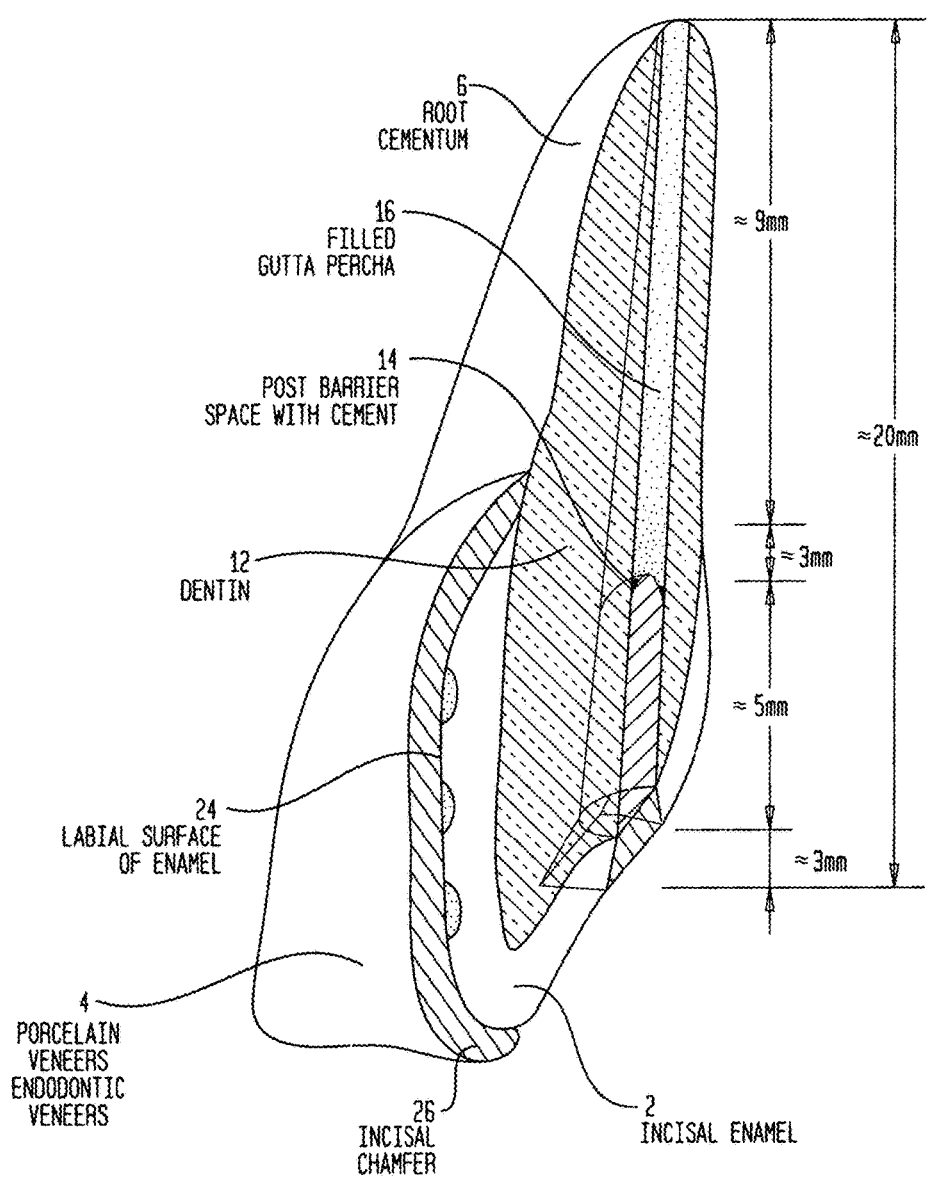

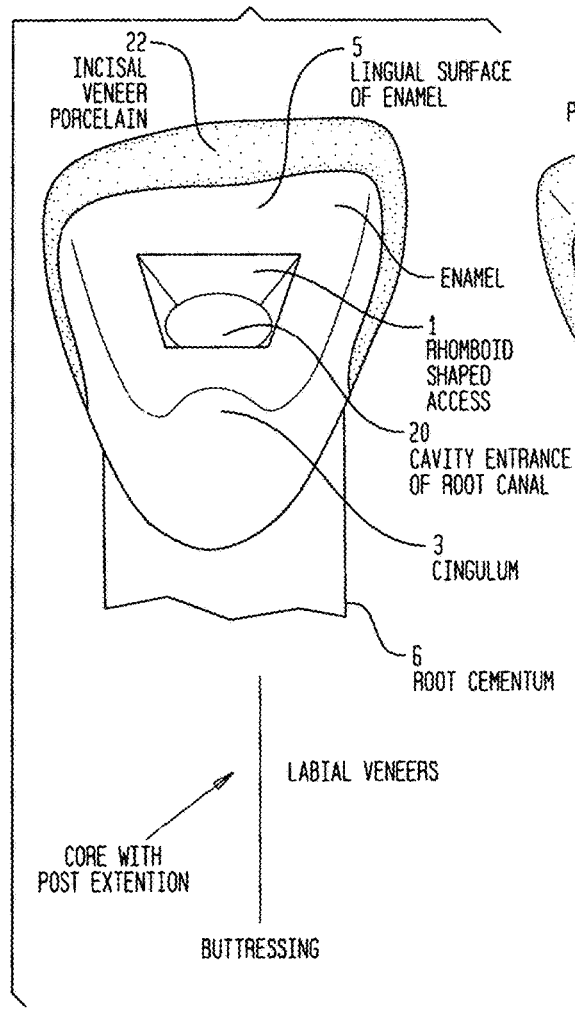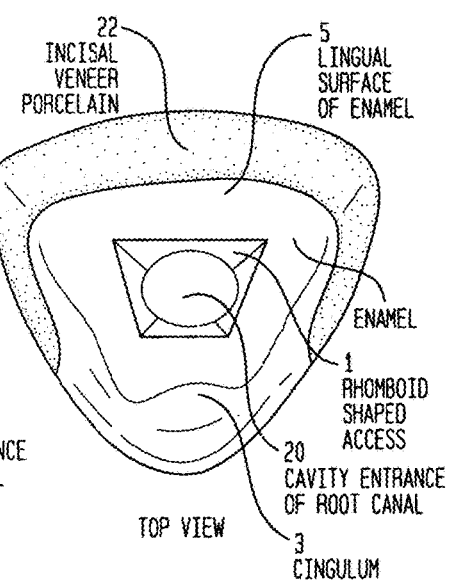

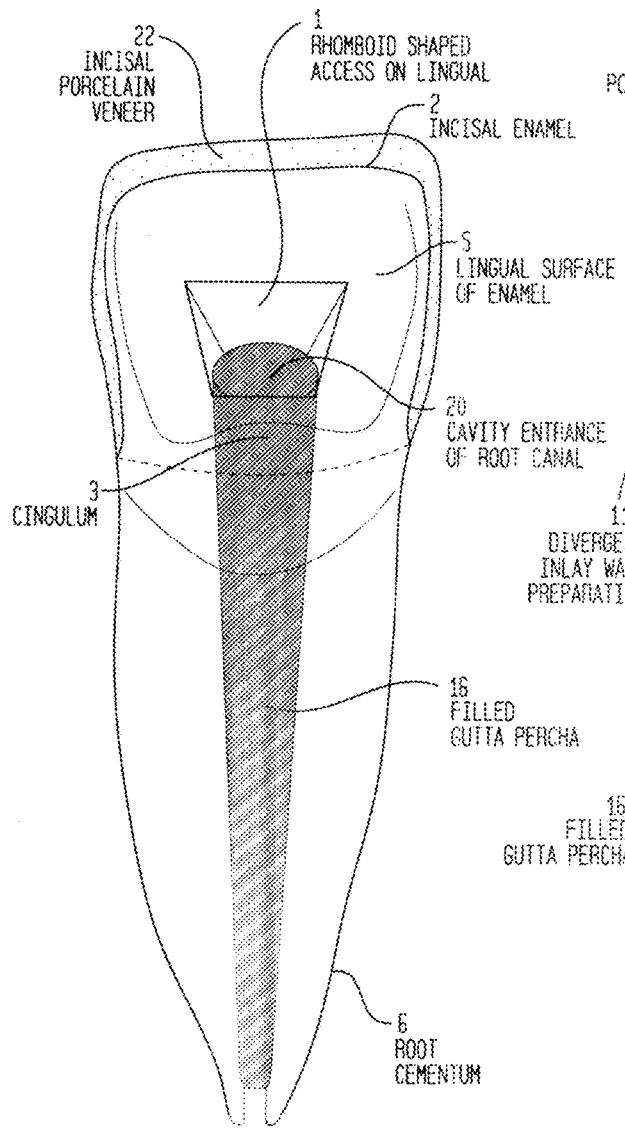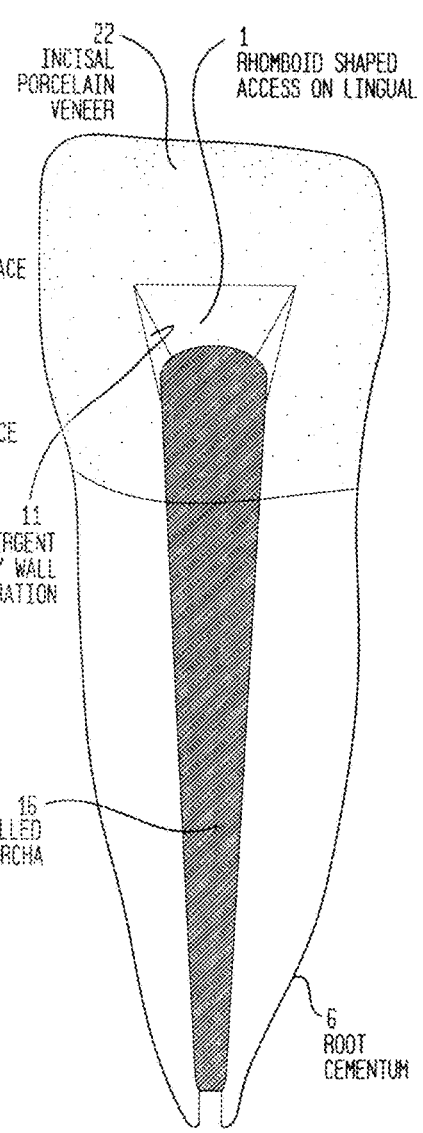

RESTORED ANTERIOR ENDODONTICALLY TREATED TEETH

RELATED PATENT APPLICATION

The present application number Ser. No. 14/569,912 is a continuation-in-part application of copending patent application Ser. No. 13/329,717, for RESTORATION OF ANTERIOR ENDODONTICALLY TREATED TEETH, filed Dec. 19, 2011, and hereby incorporates the teaching therein by reference.

FIELD OF THE INVENTION

The disclosed subject matter relates to endodontics and, more particularly, to the restored endodontically treated teeth, with porcelain facial veneer restorations.

BACKGROUND OF THE INVENTION

Endodontics or root canal therapy is that branch of dentistry that deals with the diseases of the dental pulp and periradicular tissues. One aspect of endodontics comprises the treatment of infected root canals by the removal of diseased pulp tissues, using biomechanical cleaning and shaping and subsequent filling of the pulp cavity (root canal). The access opening to the root canal must be sealed and the tooth restored. The objective in root canal therapy is to prevent leakage of toxic products from the coronal portion of the tooth infiltrating into the root canal system. The placement of the barrier material under the modified post assists in preventing the egress of microleakage through the gutta percha filling.

Root canal therapy is generally indicated for teeth having sound external structures but having diseased, dead, or dying pulp tissues. In such teeth, the pulp tissue and excised portions of the root should be replaced by a biocompatible substitute. The gold standard for filling the root canal is gutta percha and root canal sealer. Micro-leakage from the coronal portion of the tooth can pass through the gutta percha, filling to the apical portion to cause an abscess to form.

One technique for the preparation of a root canal involves creating a coronal straight line access opening with a conventional dental drill. The access opening in this technique is in the shape of an inlay preparation, in the lingual surface of the anterior tooth, to facilitate the pattern withdrawal of the orifice seal and the connected modified post extension. In posterior teeth the access preparation is made through the occlusal tooth surface. A tool is used for gross removal of pulp material from the pulp chamber through the coronal access opening. The canal orifices are located, and the canals are negotiated with narrow files to establish the glide path of the canal. These files are rotated using a balanced force technique until free access to the foramen is reached. Apex locators are used to verify the length of the instrumented canal to the apex. Hand files are used to size #20, and then followed with nickel titanium rotary systems. Debris is removed from the root canal by flushing and evacuation after each instrument use. The root canals are cleansed of all diseased tissue and pulpal remnants. Following chemical antisepsis, the instrumented canal is ready for filling.

Current techniques typically fill the root canal with gutta percha, sealer, or resin. If posts are used, they are either active or passive, metal or fiber. A cosmetic and functional crown made of porcelain fused to metal is usually attached to the post and core. The placement of metal posts can result in perforations or fractures which may contribute to later tooth damage.

DESCRIPTION OF RELATED ART

U.S. Pat. No. 4,936,776 issued to Kwiatkowski, et al. for DENTAL PRODUCT AND METHOD UTILIZING TRANSLUCENT MATERIAL issued on Jun. 26, 1990 discloses a dental product and method utilizing pre-fabricated and fabricated translucent construct (e.g., glass ionomer) as the post or post-and-core of a dental restoration. Kwiatkoski, et al. use only a facial post and core veneer.

U.S. Published Patent Application No. 2005/0227204 on an application applied for by Hauck, et al. for DAILY WEAR TEMPORARY DENTAL VENEERS published on Oct. 13, 2005 discloses a method for temporarily improving an individual's smile.

Preparing endodontically treated teeth with veneers made of very strong porcelain material allows the tooth to be kept intact. This approach provides the individual with a plurality of thin, cosmetically pleasing, veneers.

The Endodontic Veneers in this invention are prepared on the labial surface of the tooth by constructing a minimal labial chamfer in enamel of 0.5 mm and a very minimal lingual wrap over the incisal, An impression is taken from below using a formable polymeric member capable of forming a veneer impression, such as polyvinyl siloxane, PVS, IMPREGUM™ polyether dental impression material, available from 3M, Minneapolis, Minn., or other similar types of impression materials; it is sent to a dental laboratory to construct the veneer of alumina, E Max™ or zirconia porcelain.

Paint One Step Bonding agent, Prime and Bond Dentsply™ to the prepared tooth surface.

Silane Coupling Agent™ is placed on the prepared porcelain. It is the key to providing a strong chemical bond between the cement and veneer.

Light only polymerized cement such as Nexus™ is used to cement the veneer. The bonding process is finished using a curing light.

"Adapting Fiber-Reinforced Composite Root Canal Posts for Use in Noncircular-Shape Canals," by Grande, et al. in Practical Procedures in Aesthetics and Dentistry, 2006; 18(8): A-G describes a technique that adapts a preformed post to fit a noncircular-shaped root canal, starting from a commercially-available, preformed, fiber-reinforced composite root canal post to provide restoration of an endodontically-treated tooth. Grande, et al. use a pattern with patterned resin or polyvinyl siloxane.

SUMMARY OF THE INVENTION

It is an object of the disclosed invention to provide a novel method of restoring anterior and posterior endodontically treated teeth.

It is also an object of the disclosed invention to provide a method for restoring anterior and posterior endodontically treated teeth wherein the posterior end of a modified porcelain post is positioned to prevent microleakage.

It is a further an object of the disclosed subject matter to provide a method for restoring anterior endodontically treated teeth wherein a porcelain veneer is positioned on the labial surface of the tooth.

1. It is a yet further object of the disclosed subject matter to provide a method for preparing a rhomboid shaped inlay, positioned at the access opening of the root canal with a connected modified porcelain post.

It is a yet further object of the disclosed subject matter to provide a method and apparatus for restoring anterior teeth after endodontic treatment, said method and apparatus comprising:

(1) a formable polymeric member such as methyl methacrylate, or Parkell™ burn out resin, or other impression materials is used on the rhomboid inlay with a modified post extension. These materials are capable of forming a modified post and inlay core impression;

(2) The canal is lubricated with KY Jelly™ and half filled with a slurry of the impression materials, removing any excess. Use the brush dip Nelon Technique to add the methyl methacrylate or Relate™ mixture to the burn out sprue after it has been made wet with monomer. The burn out sprue is inserted into the prepared post hole to take a direct impression, taking care to avoid locking and prevent setting of material without (3) cement to prevent microleakage, forming a post barrier, such as MTA or Super EBA™ or Brassier Endo™ Sequence Repair Material, as well as any suitable cement that prevents the egress of moisture or microleakage to the apex of the root canal;

(4) Cement to cement a porcelain modified post and inlay access core in position, such as RelyX™, Ivoclar™, or Varolink™ cement; and (5) Using a bonding cement to cement a porcelain veneer, such as RelyX™, or Varolink™ cement.

The restored anterior teeth/Endodontic Veneer after endodontic treatment includes a ceramic porcelain material that, after being formed from a CAD scan or impression, aids in fabricating a labial porcelain veneer, and a rhomboid lingual access inlay of the porcelain material with an anatomical post extension connected thereto. A cement material is provided for preventing microleakage into gutta percha and for forming a post-barrier space. A porcelain inlay-shaped core includes an anatomical post extension extending from a level of an existing crest of bone of a patient into a root canal space, the length of the post extension being less than one-half the length of a root canal.

An anterior tooth is typically treated endodontically by removing the enamel and dentin tooth surfaces, causing a portal in the lingual or occlusal portion of the tooth structure, and removing diseased and/or dead nerve tissue in the root canal. The root canal is filled with material such as gutta percha, and the upper portion of the canal is finished to be continuous with the access rhomboid inlay preparation. A temporary veneer may be inserted after the labial chamfer preparation, and impression have been performed.

Intact endodontically treated anterior teeth do not need complete crown coverage unless they are weakened by large and/or multiple coronal restorations. Use of a porcelain facial veneer restoration with minimally invasive preparation, combined with insertion of an access modified post and core, is an alternative to the natural tooth with a composite access seal or to a metallic post core and crown. It is believed that porcelain veneers, such as Zirconia porcelain veneers, will support the clinical crown of an anterior endodontically treated tooth to prevent fracturing. Further support from the lingual surface, using the same material, should give additional backing to the clinical crown. The use of minimal veneer preparation along with a slight lingual wrap minimizes the amount of tooth structure that is removed. The veneer is buttressed by the lingual inlay core/modified post extension.

According to an embodiment of the disclosed subject matter, about 2 or 3 millimeters below the height of the crest of bone, the gutta percha of the endodontically treated tooth is removed to form a post space to receive a modified porcelain post. An additional about two to about three millimeters of the gutta percha is removed to accommodate the post barrier cement. The upper portion of the tooth is configured to receive a inlay core. The lingual surface of the tooth is treated to prepare the access for an anterior porcelain inlay core. A modified porcelain post and inlay core is prepared by a dental laboratory, is fitted for insertion and seal of the access preparation, and is cemented into position. The post space is prepared with Brassier Post Prep Reamers™ (Post Drills) for post space preparation or Parkell™ Endodontic Reamers A, B C (Post Drills).

The apical end of the post preparation is round. The post preparation is parallel in design. After being checked for proper insertion and fit, the modified post and inlay core is cemented into the post space preparation. The walls of the post space, and the post and inlay core, are coated with RelyX™, Ivoclar™ or Variolink™ cement prior to final insertion for cementation. These cements are beneficial in preventing microleakage and cementing porcelain restorations.

The core is the material that encircles the post after it emerges from the post space preparation into the coronal portion of the tooth. According to the disclosed subject matter, a post has some core material encircling it inside the crown, with an inlay core seal at the access opening on the lingual side of the tooth. All parts are connected and made of porcelain.

In another aspect of the disclosed subject matter, the labial and incisal surfaces of the tooth are prepared with a chamfer to receive a porcelain veneer. After the impression is taken and the veneer is made from the impression, the veneer is cemented to the indentation (chamfer preparation).

According to an embodiment of the disclosed subject matter, a cement is used in the lower portion of the root canal as a barrier to micro-leakage. This cement also provides a stable anchor for a porcelain fabricated post. The porcelain core and post are used to support the facial tooth and veneer.

The modified post and inlay core and the porcelain veneers are preferably fabricated with the aid of 3-dimensional imaging software. This technology offers anterior tooth restoration that prevents micro-leakage and reduces stress on the root walls.

More particularly, the procedures according to the disclosed subject matter combine existing imaging and fabrication technologies and cements in a novel procedure to restore anterior teeth after root canal. Reproduction of veneers and an inlay core with modified post can also be fabricated by using the IPS E Max Ceram™ layering, ceramic and other porcelain materials.

The disclosed subject matter may be better implemented with the development of advanced scanning probes that can scan into the root canal. Such scanning probes would be thin enough to scan the inlay core and post preparation. A very thin probe should be developed to capture the image of the post preparation in the root canal space, along with development of software that can read the scans taken and reproduce them in porcelain cutting machines. This will enable the reproduction of the post/rhomboid inlay shaped core with hardware provided for porcelain reproduction in the office. It would not be necessary to send materials to a laboratory for a direct cast reproduction, resulting in a savings of time and money.

Overall, the technology disclosed and used herein is less invasive and requires the removal of less tooth structure than current technology for restoring anterior teeth after endodontic treatment.

The instant technique includes:
- injecting a cement barrier, for example, of from about 2 to about 3 mm of MTA, Super EBA™, or Brassier Root Canal Apico™ Cement into the root canal to prevent bacterial micro-leakage;
- injecting a second cement capable of bonding the modified post and inlay core to the root canal, such as a RelyX™, Ivoclar™, or Variolink™ cement;
- inserting the apical end of the modified post and inlay core into the root canal to contact the post barrier cement;
- smoothing the occlusal end of the modified post and rhomboid shaped inlay core to be co-extensive with the lingual surface of the tooth;
- removing from about 0.2 to about 0.3 mm of enamel from the labial and about 0.2 mm from the incisal surfaces of the tooth to prepare a chamfer to receive the margin outline of the porcelain veneer;
- taking an impression of the veneer preparation;
- having a lab prepare a temporary plastic veneer with a selected shade until the final veneer is completed;
- cementing with spot cementation on the labial preparation;
- pumicing off after temporary plastic veneer is removed and permanent veneers are tried into place;
- preparing a porcelain veneer from the impression of the veneer preparation; and
- cementing the porcelain veneer into the veneer preparation, by isolating with rubber dam, and placing plumber's tape and paper points interproximally.

In one aspect of the disclosed subject matter, a basic tray for the porcelain veneer, comprises a Brasseler Laminate Burs Kit™, Diamond Chamfer Burs, vacuum-formed stent for transportation of putty index, VPS light body and medium body material, Impregum™, Poly Vinyl Siloxane Impression Cement, to take an impression using dental impression trays to incorporate the preparation for reproduction. Order a lab preparation with the taken impression to construct a labial veneer with EMAX™ or zirconia porcelain.

In another aspect for delivery, a basic tray comprises One Step™ bonding agent, Prime and Bond™ by Dentsply™ on the facial veneer preparation, etching the porcelain veneer with 9.6% hydrofluoric acid, using highly filled flowable resin or a conventional resin composite cement to cement the veneer. The placement of a silane coupling agent is the key to providing a strong chemical bond between the cement and veneer. Place it on the prepared porcelain. Follow the manufacturer's recommendation for length of time placement of the silane. Use resin cement to cement the veneers anterior and posterior post/inlay Light Cure Type Nexus™, VarioLink™ finishing burs (Brasseler Laminate Burs Kit™), and interproximal serrated strips.

Kit Preparation Guide for Endodontic Veneers with Modified Inlay and Post Extension With the Rhomboid Lingual Access preparation extending into the root canal opening, prepare inlay walls for impression withdrawal (divergent)

An inlay preparation is made with the modified post extension (preparation).

Use Brasseler™ Post Prep Reamers (Post Drills) or Parkell™ Endodontic Reamers A,B,C (Post Drills) for the post space preparation.

Prepare and remove the gutta percha in the root canal initially (Use Parkell A, 2 bladed, Gates™ burs or Brassler™ Post Drills).

Use a Rubber Stopper on the Post Drills to establish measurement control.

The depth of the post hole is determined by the length of root, position of the bone crest, and the root wall thickness.

Post preparation is not a full post space preparation, but it is modified to extend the length of 2 mm below the crest of the existing bone left.

Allow 2 mm extra post space for the insertion of the Post Space Barrier, using Super EBA Cement™ or Brassier Root Canal Apico™ cement.

Use a parallel sided preparation or a tapered depth preparation. Use appropriate post drills to create a final taper or a parallel preparation.

Use KY™ Jelly to lubricate the canal.

The plastic sprue (Burn Out Post and Core Pattern) is cut to fit the canal loosely to form a direct post pattern.

Use methyl methacrylate to take an impression of the post space preparation and the Occlusal™ inlay preparation Liquid Monomer and Powder, or use Parkell Relate™ Blue Burn Out Resin™.

After lubrication with KY Jelly™, the canal is half-filled with methyl methacrylate or Relate™ (a soupy mix).

Remove any excess.

Use a brush dip Nelson technique to add the methyl methacrylate or Relate™ mixture to the burn out sprue after it has been made wet with monomer Super EBA™ cement or use Brasseler™ Endo Sequence Root Repair™ material for the post space barrier.

Insert into the post hole and move in and out to avoid locking and to prevent setting of material without being able to withdraw.

The material should fill the rhomboid shaped inlay space preparation filling in all margins on the lingual surface of the tooth.

After completely set, withdraw and send to a lab for fabrication. This reproduces the modified inlay with post extension.

Isolate the prepared tooth with a rubber dam.

Remove bacteria on the surface of the preparation by painting with Chlorhexidine™.

Remove any excess with air.

Add 2 mm of Super EBA™ or Brasseler™ Endo Sequence Repair Material using a syringe for the post space barrier.

Etch the porcelain inlay preparation with post extension with 9.6% hydrofluoric acid.

Cement the inlay preparation with the modified post extension using Light Only Polymerized Cement™.

Preparation of Labial Veneer for Ceramic Porcelain Veneer

Construct a minimal labial chamfer veneer preparation of 0.5 mm with a very slight lingual wrap in enamel on the labial portion of the endodontically treated tooth. The entire lingual wall is not reduced and kept intact except for the rhomboid access inlay preparation which was made to access the root canal treatment.

Complete the preparation.

Isolate the prepared tooth with a rubber dam.

Remove bacteria on the surface of the preparation by painting with Chlorhexidine™.

Remove excess with air and take an impression using rubber cement or polyvinyl siloxane impression cement using dental impression trays to incorporate the preparation for the reproduction.

Order a lab preparation with the taken impression to construct a labial veneer with alumina, E MAX™ or zirconia porcelain.

Acid etching the labial tooth surface is used ONLY with silica based ceramics not with zirconia or E MAX™.

Use One Step™ bonding agent, Prime and Bond™ by Dentsply™

Etch the porcelain veneer with 9.6% hydrofluoric acid.

Use highly filled flowable resin or a conventional resin composite cement to also cement the veneer.

The placement of a silane coupling agent is the key to providing a strong chemical bond between the cement and veneer. Place it on the prepared porcelain.

Follow manufacturer's recommendation for the length of time placement of the silane.

Use Light Only Polymerized Cement™ to cement the veneer.

Use Nexus Clear™ (by Kerr) base cement to load the veneer. If the veneer is very opaque, use a catalyst.

Place a floss interproximally between the mesial and the distal of the prepared tooth.

Tack each veneer.

Pull the floss lingually to remove excess of the cement.

Remove excess cement from veneers prior to doing final bonding.

Finish the bonding process with curing light.

The veneer is finally cemented.

In another aspect of the disclosed subject matter, the elements for restoring anterior teeth after endodontic treatment comprise:
(1) a formable polymeric member capable of making a modified post and inlay core impression; and
(2) a formable polymeric member capable of forming a veneer impression.

In another aspect of the elements of the disclosed subject matter, the formable polymeric member comprises methyl methacrylate or Parkell Relate™ Blue Burn Out Resin™ which is used similarly.

In another aspect of the elements of the disclosed subject matter, the formable polymeric member comprises polyvinyl siloxane or Impregum™.

In another aspect of the elements of the disclosed subject matter, the method and apparatus further comprises cement capable of preventing microleakage.

In another aspect of the elements of the disclosed subject matter, the cement is MTA Super EBA™ cement or Brasseler Root Canal Apico™ cement, In another aspect of the elements of the disclosed subject matter, the elements further comprise cement capable of cementing a porcelain modified post and inlay in position and of cementing a porcelain veneer.

In another aspect of the elements of the disclosed subject matter, the cement is Nexus Clear (Kerr)™ base cement, RelyX™, Ivoclar™, or Variolink™ cement. Use Nexus Clear (Kerr)™ base cement.

In another aspect of the elements of the disclosed subject matter, the elements further comprise Brasseler™ abrasive drill bits.

In another aspect of the elements of the disclosed subject matter, the elements further comprise porcelain substrates.

In another aspect of the elements of the disclosed subject matter, the elements for restoring anterior teeth after endodontic treatment comprise:
(1) a formable polymeric member capable of making a modified post and inlay core impression;
(2) a formable polymeric member capable of forming a veneer impression; and
(3) a cement capable of preventing microleakage.

In another aspect of the disclosed subject matter, a method of restoring an anterior endodontically treated tooth having labial, incisal, and lingual surfaces comprises:
inserting a formable polymeric member into a root canal directly, to make an impression from the root canal suitable for forming a porcelain modified post and inlay core;
inserting a porcelain modified post and inlay into the root canal;
taking an impression of a modified veneer surface with a formable polymeric member for forming a porcelain veneer; and
cementing the porcelain veneer into the modified veneer surface.

In another aspect of a method of the disclosed subject matter, the method further comprises preparing a porcelain modified post and inlay core from the formable member, the porcelain modified post and inlay core having an apical end and an occlusal end containing an inlay.

In another aspect of a method of the disclosed subject matter, the method further comprises injecting a portion of a first cement which prevents the egress of moisture through the gutta percha filling into the root canal to form a barrier to prevent microleakage.

In another aspect of a method of the disclosed subject matter, the method further comprises injecting a portion of a second cement into the root canal capable of bonding the modified post and inlay core to the root canal.

In another aspect of a method of the disclosed subject matter, the method further comprises injecting cement into the root canal to form a barrier to prevent microleakage and to bond the modified post and inlay core to the root canal.

In another aspect of a method of the disclosed subject matter, the method further comprises inserting into the root canal a porcelain modified post and inlay core to contact portions of first and second cements.

In another aspect of a method of the disclosed subject matter, the method further comprises smoothing an occlusal end of the modified post and inlay core to be co-extensive with the lingual surface of the tooth.

In another aspect of a method of the disclosed subject matter, the method further comprises removing a portion of the labial and incisal surfaces to create a chamfer.

In another aspect of a method of the disclosed subject matter, the method further comprises preparing a temporary plastic veneer with a selected shade until a final veneer is completed.

In another aspect of a method of the disclosed subject matter, the method further comprises cementing with spot cementation on the labial preparation.

In another aspect of a method of the disclosed subject matter, the method further comprises pumicing off after a temporary plastic veneer is removed and a permanent veneer is tried into place.

In another aspect of a method of the disclosed subject matter, the method further comprises preparing a porcelain veneer from the impression of the modified veneer surface.

In another aspect of a method of the disclosed subject matter, the method further comprises cementing the porcelain veneer into the modified veneer surface.

In another aspect of a method of the disclosed subject matter, when the root canal is filled with gutta percha, the method further comprises removing most of the gutta percha from the root canal to provide a post space for a formable polymeric member capable of forming a modified post and inlay core impression.

In another aspect of a method of the disclosed subject matter, the formable polymeric member comprises methyl methacrylate or Relate™ Blue Burn Out Resin™ (by Parkell).

In another aspect of a method of the disclosed subject matter, the method further comprises preparing a chamfer by removing from about 0.2 to about 0.3 mm of enamel from the labial surface of the tooth and about 0.2 mm from the incisal surface of the tooth.

In another aspect of a method of the disclosed subject matter, the porcelain veneer is cemented into the veneer preparation by isolating the proximal portion of the tooth with plumber's tape and paper points interproximally.

In another aspect the disclosed subject matter, a method of restoring an anterior endodontically treated tooth having labial, incisal, and lingual surfaces and having a root canal filled with gutta percha and extending from the lingual surface comprises:

removing a portion of the gutta percha from the root canal to provide a post space for a formable polymeric member capable of forming a modified post and inlay core impression;

inserting a formable polymeric member into the root canal to make an impression from the root canal suitable for forming a porcelain modified post and inlay core;

preparing a porcelain modified post and inlay core from the formable member, the porcelain modified post and inlay core having an apical end and an occlusal end containing the inlay;

injecting cement into the root canal to form a barrier to prevent microleakage and to form a ferrule in cement with the modified post and inlay core in the root canal;

inserting the porcelain modified post and inlay core into the root canal to contact the cement;

smoothing the occlusal end of the modified post and inlay core to be co-extensive with the lingual surface of the tooth;

removing a portion of the labial and incisal surfaces to create a modified veneer surface with a chamfer to receive the margin outline of a porcelain veneer;

taking an impression of the modified veneer surface;

preparing a temporary plastic veneer with a selected shade until a final porcelain veneer is completed;

cementing with spot cementation on the labial preparation;

preparing a porcelain veneer from the impression of the veneer preparation;

pumicing off after temporary plastic veneer is removed and the final veneer is tried into place; and cementing the porcelain veneer into the modified veneer surface.

In another aspect of a method of the disclosed subject matter, a first cement is inserted into the root canal to form a barrier to prevent microleakage.

In another aspect of a method of the disclosed subject matter, the first cement barrier comprises from about 2 to about 3 mm of MTA or Super EBA™ cement or Brassler Root Canal Apico™ cement.

In another aspect of a method of the disclosed subject matter, a second cement is inserted to bond the modified post and inlay core to the root canal.

In another aspect of a method of the disclosed subject matter, the use of a strong silane coupling agent and a light only polymerized cement, Kerr Nexus Clear base cement™ to provide a strong chemical bond for cementation of the laminate porcelain veneer. Other cements comprise RelyX™, Ivoclar™, or Variolink™ cement.

In another aspect of a method of the disclosed subject matter, the chamfer is prepared by removing from about 0.2 to about 0.3 mm of enamel from the labial surface of the tooth and about 0.2 mm from the incisal surface of the tooth.

In another aspect of a method of the disclosed subject matter, the laminate porcelain veneer is cemented into the modified veneer surface by isolating the proximal portion of the tooth with plumber's tape and paper points interproximally.

In another aspect of disclosed subject matter, a method of treating a tooth after endodontic treatment comprises inserting into a root canal an effective amount of a cement capable of preventing egress of moisture or microleakage to the apex of the root canal.

In another aspect of a method of the disclosed subject matter, the cement is Super EBA or MTA™ or Brasseler Root Canal Apico™ cement.

While the technology disclosed and used herein primarily pertains to the treatment of anterior endodontically treated teeth, the principles here are also applicable to the treatment of posterior endodontically treated teeth.

These and other objects and advantages of the present invention are more readily apparent with reference to the following detailed description and the accompanying drawings.

In accordance with the present invention, there is provided a restored anterior teeth/endodontic veneer after endodontic treatment. A ceramic porcelain material is provided that, after being formed from a CAD scan or impression, aids in fabricating a labial porcelain veneer and a rhomboid lingual access inlay of the porcelain material with an anatomical post extension connected thereto. A cement material is provided for preventing microleakage into gutta percha and for forming a post-barrier space. A porcelain inlay-shaped core is provided comprising an anatomical post extension extending from a level of an existing crest of bone of a patient into a root canal space, the length of the post extension being less than one-half the length of a root canal.

BRIEF DESCRIPTION OF THE DRAWINGS

A complete understanding of the present invention may be obtained by reference to the accompanying drawings, when considered in conjunction with the subsequent detailed description, in which:

FIG. 1 is a cross-sectional view of an anterior tooth that has been endodontically treated;

FIG. 2 is a cross-sectional view of the tooth in FIG. 1 where the tooth has been prepared to take an impression.

FIG. 3 is a cross-sectional view of the tooth in FIG. 2 where an impression is being taken;

FIG. 4 is a cross-sectional view of the tooth of FIG. 3 where the modified post and inlay core and the veneer inlay has been inserted;

FIG. 5 is a another cross-sectional view of the tooth of FIG. 4;

FIG. 6 is a top view of the tooth of FIG. 4; and

FIG. 7 is another top view of the tooth of FIG. 4.

FIG. 8 a lingual view of a tooth

FIG. 9 a labial view of a tooth

Like reference numerals refer to like parts throughout the several views of the drawings. Please use legend to identify the parts of the drawings.

DETAILED DESCRIPTION OF THE PREFERRED EMBODIMENT

Although the following detailed description contains specific details for the purposes of illustration, those of ordinary skill in the art will appreciate that variations and alterations to the following details are within the scope of the invention. Accordingly, the exemplary embodiments of the invention described below are set forth without any loss of generality to, and without imposing limitations upon, the invention.

Restored anterior teeth/endodontic veneer after endodontic treatment has a ceramic porcelain material that, after being formed from a CAD scan or impression, aids in fabricating a labial porcelain veneer and a rhomboid lingual access inlay of the porcelain material with an anatomical post extension connected thereto. A cement material is provided for preventing microleakage into gutta percha and for forming a post-barrier space.

The preferred embodiments of the disclosed subject matter will now be described with reference to the drawings. Identical elements in the various figures are designated with the same reference numerals.

FIG. 1 illustrates a cross-sectional view of an endodontically prepared anterior tooth prior to further processing. A tooth has a cingulum 3, gingival margin 9, crown 8 and a root 17. Crown 8 comprises enamel 24, and dentin 12. Tooth has a root canal 16 that is filled with gutta percha and cement 14, such as Columbia cement. The cement fills cavity 15.

In the cross-sectional view of FIG. 2, cement 14 and a calibrated amount of gutta percha have been removed from root canal 16. An indentation chamfer preparation 13 has been created in enamel on a labial surface 24 and an incisal surface 26, to a depth of from about 0.3 mm to about 0.5 mm. The upper edge 32 of the indentation 30 ends approximately about 2 mm to about 3 mm from the upper edge 32 of cavity 20.

A formable polymeric member 36, which has a sprue 38, is lubricated with a DURALAY™ Tin Lubricant or a petroleum-based lubricant product such as Vaseline petroleum jelly KY™ Jelly and then inserted into cavity 20 and root canal 16, as shown in FIG. 3. The impression material is withdrawn slowly and reinserted to prevent permanent locking. Once polymeric member 36 hardens, it is used to form a modified post and inlay core 52. In one aspect of the invention, a modified post and inlay core is prepared scanning the impression, and using CEREC 3-D software, as described herein below.

The apical end 42a of polymeric member 36 is positioned (for example, by X-ray) about 2 mm to about 3 mm below the height of the crest bone 44 of the collar of the tooth between enamel and root 16. There is a gap in the root canal 16 of about 2 mm between apical end 42a and the remaining gutta percha, which is more than 4 mm in length.

A formable member (not shown) is also used to form a veneer 4 to fill the chamfer indentation 22. The final porcelain veneer, with lingual support members, is formed, for example, using CEREC 3-D software or scanning and reproducing.

FIG. 3 shows a cross-sectional view of the tooth in FIG. 2 where an impression is being taken of the rhomboid shaped inlay core and modified post extension.

FIG. 4 shows a cross-sectional view of the tooth of FIG. 3 where the post extension member 52 comprising the modified post and rhomboid shaped inlay core and the veneer 4 (shown in FIG. 5) have been inserted.

FIG. 5 is another cross-sectional view of the tooth of FIG. 4, showing the labial porcelain veneer 4, the rhomboid access 1, the modified post extension 52, which goes 2-3 mm into the post barrier space 15. This space contains the post barrier cement 14.

FIG. 6 is a lingual view of the tooth of FIG. 4, showing the incisal porcelain 22, the lingual enamel surface 2, the rhomboid access preparation 1, and root canal orifice cavity 20.

FIG. 7 is another top view of the lingual aspect of the tooth of FIG. 4. This view depicts a deeper view of the rhomboid shaped inlay access 1 extending into the root canal orifice cavity 20.

To prepare a final tooth according to the disclosed subject matter, post barrier cement 14 to prevent bacterial microleakage is injected or inserted into the 2-3 mm open space proximal to the gutta percha in the root canal 16 and the post barrier space 15 as shown in FIG. 4, the post 52 being no greater than one half the length of root canal 16. Also, a veneer 4 has been cemented into labial surface indentation 24.

The facial and incisal surfaces of teeth are prepared minimally into enamel and the access opening 1 of the root canal 16, and closed with an inlay core preparation and a modified post preparation made of the same materials. These give additional support to the clinical crown 8 and prevent fracturing. The modified post is seated into a post barrier cement 14 of Super EBA™ MTA™ Brasseler Root Canal Apico Cement™ or any suitable cement that prevents the egress of moisture or microleakage to the apex of the root canal.

According to the disclosed subject matter, the modified post and inlay core and the labial veneer member are prepared from suitable porcelain, preferably using zirconia or alumina porcelain or EMAX™. This porcelain can comprise zirconia oxide, yttrium oxide, and cerium oxide. Other suitable porcelain materials such as IPS EMAX™ Ceram layering ceramic can also be used. yttrium oxide, and cerium oxide. Other suitable porcelain materials such as IPS EMAX™ Ceram layering ceramic can also be used.

Various cements are useful according to the disclosed subject matter. A particularly important cement is the one that is injected into the root canal space apical to the terminus of the modified porcelain post 52 to prevent the egress of moisture, that is, microleakage, into the root canal. Suitable cements for this purpose include Super EBA™ available from Bosworth or mineral trioxide aggregate (MTA), available from Dentsply™ and Brassier Root Canal Apico™ cement. Other cements that prevent the egress of moisture or microleakage can be substituted. These cements have been clinically proven to be successful apical sealers in apicoectomy surgical procedures. Prior to cementation, the post space barrier cement 14a is inserted into the root canal space with a syringe. Any suitable carrier can also be substituted to place the cement barrier into the root canal.

Other cements or bonding agents are useful to cement the modified post and inlay core 52 include, but are not limited to, light only polymerized cement, Nexus™ and RelyX™ (from 3M), Ivoclar™, and Variolink™.

Preparation of the indentation for the porcelain veneer is preferably accomplished with diamond Brasseler™ burs. The depth burs are applied to the labial (front surface) and incisal surfaces of an anterior tooth to prepare a reduction of enamel that is uniformly from about 0.3 to about 0.5 mm deep on the labial surface and about 0.3 or less deep on the incisal surface. This allows space for the porcelain to be continuous and wrap around the labial porcelain. Caution must be applied not to cut through to the enamel surface of the tooth. A sharply demarcated chamfer (edge or groove) is prepared on the proximals, gingival margin, and at the terminus of the incisal preparation on the lingual side of the tooth. This permits the wraparound of the porcelain over the incisal to the lingual side of the tooth. The incisal may not have to be prepared with a wraparound of the labial porcelain. The edge or groove (chamfer) defines the enamel reduction. The veneer is prepared from PVS (polyvinyl siloxane) impressions of the tooth. This impression is sent to a dental laboratory to prepare the temporary and final veneers. Teeth may be left uncovered or covered with temporary restorations until the final veneer has been fabricated. The final porcelain veneer can also be formed in the dental office from a hard solid porcelain block using three-dimensional software, CEREC, an acronym for Chair side Economical Restoration of Esthetic Ceramics, such as described above. The prepared tooth can be restored in a single visit appointment with no need to construct temporaries or have lab fees.

As described hereinabove, a ceramic porcelain material is introduced that, after being formed from a CAD scan or impression, aids in fabricating a labial porcelain veneer 4 and a rhomboid lingual access inlay 1 of the porcelain material with an anatomical post extension connected thereto 52. A Brasseler™ reamer or Parkell™ C-1 reamer is used to remove gutta percha, and additional gutta percha is removed for placing a post barrier space cement comprising MTA™ or Super EBA™ cement. Approximately 2-3 mm of gutta percha below the height of the crest of existing bone, are initially removed for post space preparation and an additional 2 mm of gutta percha are removed for the Super EBA™, Brasseler Endo Sequence Repair Material™ as post barrier material. The post space barrier cement is inserted into the root canal space prior to cementation with a syringe and the ceramic porcelain facial veneer and porcelain inlay with modified post are cemented using Nexus™ or any other light polymerized cement. The modified post is placed to imprint itself into the barrier material.

In preparing the modified post space use parallel sided or tapered depth preparation creating a parallel sided or parallel preparation. The space is lubricated with KY™ Jelly, Duralay lubricant DURALAY™ polyacrylic resin, available from Reliance Dental Mfg. Co., of Alsip, Ill. A plastic sprue 38 (Burn out Post and Core Pattern or Relate™ Blue Burn Out Resin) is cut to fit the canal loosely and adjust to a length 2 mm short of contact with said gutta percha to form a DIRECT post pattern. Half fill the canal with methyl methacrylate or Relate™ Parkell Blue Burn Out Resin (a soupy mix) Use a brush dip Nelson technique to add the methyl methacrylate or Relate™ burn out sprue after it has been made wet with monomer. Insert into the post space and move in and out to avoid locking. The impression material is extended to cover the inlay core preparation, filling in all margins of the tooth. After completely set, withdraw and send to a laboratory to fabricate a porcelain inlay core with a post extension.

An impression is taken using polyvinylsiloxane or Impregum Cement™ of the chamfer preparation for forming a ceramic porcelain veneer 4. Using a porcelain selection of EMAX™ zirconia or alumina porcelain, Light Only Polymerized Cement™ or any other similar type to form the veneer. Upon completion, it is cemented on to the prepared tooth surface using Nexus Clear™, or any other type of Light Only Polymerized Cement™.

As described hereinabove, a polymeric form 36 is inserted into the root canal 16 to form an impression to be used to prepare the modified post and inlay core 52. There are a number of polymeric materials that are known to be useful for this purpose. A preferred material is DURALAY™ polyacrylic resin, available from Reliance Dental Mfg. Co., of Alsip, Ill. Another material is Parkell Relate™ Blue Burn Out Resin.

A Study Applying the Invention to Extracted Human and Plastic Model Teeth

The purpose of a study was to construct an alternative model restoration for an anterior endodontically treated tooth. By constructing a minimal veneer preparation of about 0.5 mm or less, the intent is to reduce the amount of tooth structure and restore it with a strong porcelain veneer. It would be buttressed by a lingual inlay shaped core/modified post restoration to prevent the shearing of the clinical crown at the cervical.

Materials and Method: A total of twenty-four root canal treated anterior teeth were instrumented, filled with gutta percha and sealer, and prepared minimally for facial veneers. Gutta percha was removed from the root canal space to allow for modified post placement and post space barrier. A post space preparation was made using a Brasseler™ Para Post non-end cutting, domed shaped Peezo Bur™. Super EBA™ cement and MTA cement were used as the post space barrier material. Previous microleakage studies showed these materials to be resistant to the penetration of microleakage.

Of the twenty-four teeth, sixteen teeth were plastic typodont, and eight were extracted human anterior teeth. Brasseler™ depth cut burs were used to remain in enamel and reduce only enough tooth structure so that approximately 0.3-0.5 mm of labial enamel and 0.5 mm of incisal enamel was removed. Twenty-four teeth were prepared for a inlay core access with a modified post preparation of approximately 3 mm. A pattern of the inlay core and modified post was constructed from DURALAY™ polyacrylic. Three zirconia-like modified post and inlay core restorations were fabricated directly, each tooth using CEREC 3-D Software, which is WINDOWS®-based and three-dimensional. Unlike other restorative methods, this procedure provides maximum control and vision, allowing views of the preparation from all angles.

The CEREC 3-D software is available from Sirona Dental Systems.

According to MobileTekLabs, the procedure for constructing a porcelain facial veneer with the CEREC 3-D software is as follows:

Step 1: Start a new restoration.
Step 2: Choose Veneer mode (an anterior tooth must be chosen in order to utilize Veneer mode).
Step 3: Powder the cavity of the tooth.
Step 4: Take an unobstructed image of the cavity; press the green arrow.
Step 5: There is no need to trim the image; press the green arrow.
Step 6: Mark the margin; press the green arrow.
Step 7: A veneer outlined in green will appear. The green outline needs to be the same shape as the margin. Adjust the green line incrementally until it is the same shape as the margin. The final shape needs to be slightly smaller in diameter then the margin; press the green arrow.
Step 8: Use the form tool to apply 1 mm of material to the surface of the restoration. (This will ensure the sprue is placed in an optimal position.) Press the green arrow.
Step 9: Mill the restoration.

Six porcelain facial veneers were constructed from the CEREC 3D software.

In another procedure, the DURALAY™ impression of the inlay core and modified post impression is sent to a lab where an EMax™ Porcelain casting can be made and the porcelain reproduction returned for cementation.

Three millimeters of gutta-percha were removed for the post space preparation, and an additional 2 mm were removed for the Super EBA™ post barrier material. MTA cement was also used as a barrier cement material.

The porcelain facial veneer, and porcelain inlay core with modified post were cemented using Ivoclar™ or Variolink™ cement. Any suitable cement for veneer cementation can be substituted. The modified post is placed to imprint itself into the post space barrier material. This procedure can be checked with a radiograph prior to final cementation.

Results and Conclusions: Although stress tests were not conducted in this study, a review of the literature would support the use of zirconia-like porcelain veneers to be a useful alternative in restoring endodontically treated teeth. Zirconia is superior strength as a restorative material lends itself to be used without removing excess tooth structure. The replacement of cast and prefabricated metal posts which lead to micro fractures and failures with zirconia-like porcelain a plausible alternative. This is a first time presentation of using porcelain facial veneer restorations supported by a lingual inlay core and modified post with endodontically treated teeth. A similar application to this procedure can be applied to posterior teeth with the inlay core/modified post on the occlusal access preparation of endodontically treated teeth.

While various descriptions of the present invention are described above, it should be understood that the various features can be used singly or in any combination thereof. Therefore, the invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. All such modifications, variations and other uses and applications which do not depart from the spirit and scope of the invention are deemed to be covered by the invention, which is defined as set forth in the claims which follow.

Since other modifications and changes varied to fit particular operating requirements and environments will be apparent to those skilled in the art, the invention is not considered limited to the example chosen for purposes of disclosure and covers all changes and modifications which do not constitute departures from the true spirit and scope of this invention.

Having thus described the invention, what is desired to be protected by Letters Patent is presented in the subsequently appended claims.

What is claimed is:

1. A dental system for use in the formation of a dental restoration of an anterior tooth treated for a root canal,
    wherein the anterior tooth has a veneer prepared enamel body, a labial side, a lingual side, a top side, an incisal side, a drilled canal, wherein the drilled canal has an orifice and an apical end, and is partially filled with a filler, the dental system comprises:
    a barrier cement member configured to be positioned at a first exposed surface of the apical end of the drilled canal, wherein the barrier member has a thickness of about 2 mm to about 3 mm, wherein the barrier member comprises a stopper for the apical end of the drilled canal;
    wherein the barrier cement member is capable of preventing micro-leakage through the filler in the apical canal,
    a post member with a body configured to be positioned axially in the drilled canal, the post member comprises a coronal end located on the lingual side of the body, a terminal end to be positioned at the end of the first exposed surface of the drilled canal, the terminal end of the post member is configured to insert into the barrier member,
    wherein the post member and the barrier member are contiguous with each other to form a modified post assembly,
    an inlay core member configured to be positioned on a second exposed surface located on the lingual side of the enamel body, the inlay core member contains an apical end and an occlusal end,
    wherein the inlay core member comprises a shape chosen from a rhomboid or trapezoid;
    wherein the apical end of the inlay core member is axially attached to the coronal end of the post member to form an extension post assembly;
    a veneer configured to be positioned on the labial side of the enamel body,
    wherein the veneer has an enamel-facing side, a top edge, and a labial side, wherein the top edge and the labial-side of the veneer is configured to cover an entire portion of a prepared enamel body including an incisal edge,
    wherein the veneer has an average thickness of about 0.2 mm to 0.3 mm on the labial side of for covering the veneer prepared enamel body and a thickness of about 0.2 mm wherein the top edge and the labial side of the veneer is configured to sit flush with an indentation on the labial and incisal side of the veneer prepared enamel body;
    wherein the veneer is further configured to be positioned on the incisal side of the veneer prepared enamel body comprising a wrap-around of about 0.2 mm on the incisal side;
    wherein the veneer comprises a material selected from a group consisting of glass ceramic, lithium disilicate, zirconia, partially stabilized zirconia, alumina stabilized zirconia and alumina and a mixture thereof.

2. The dental system according to claim 1, wherein the veneer is buttressed with the inlay core member and the extension post assembly.

3. The dental system according to claim 1, wherein the barrier member further comprise a bioceramic root repair material selected from a group consisting of an alumina-fortified material and a mineral trioxide aggregate.

4. The dental system according to claim 1, wherein the post extension assembly forms a continuous member with the inlay core member.

5. The dental system according to claim 1, wherein the inlay core member is axially attached to the post extension assembly to form a connection configured to form a seal with a plurality of margins on an exposed surface of the lingual side of the veneer prepared body.

6. The dental system according to claim 1, wherein the inlay core member comprises materials selected from a group consisting of glass ceramic, di-lithium sillicate, zirconia, and other suitable porcelain materials.

7. The dental system according to claim 1, wherein the post extension assembly—has a length of at least about 5 mm.

8. The dental system according to claim 1, further comprising a kit for use in an endodontic treatment of a tooth treated for a root canal, for taking a direct dental impression of the drilled shaft, the kit comprising:
   a first formable polymeric member capable of taking an impression of the drilled shaft partially filled with a filler, wherein the first formable polymeric member comprises a methyl methacrylate resin a second polymeric member capable of forming an impression of an exposed surface positioned of the lingual side of the enamel body,
   wherein the second polymeric member comprises polyvinylsiloxane and or a rubber-based cement;
   a third formable member capable of forming an impression for a veneer on an exposed surface of the labial side of the enamel body.

9. A dental system for use in the restoration for an anterior tooth treated for a root canal, wherein the tooth has a lingual side, a labile side, a top side, an incisal side and a drilled canal, wherein the drilled canal has an orifice and an apical end, has a plurality of margins, and is partially filled with a filler; the dental system comprises:
   a post member having a coronal end and a bottom end,
   a barrier member configured to be positioned at the apical end of the drilled canal,
      wherein the barrier member comprises a stopper for the apical end of the drilled canal;
      wherein the barrier member is capable of preventing microleakage through the filler in the drilled canal;
   wherein the post member is configured to be anchored into the barrier member,
   an inlay core to be positioned on the coronal end of the post member,
   wherein the inlay core has a bottom end and a top end;
   wherein the bottom end of the inlay core member is configured to be axially attached to the coronal end of the post member;
   wherein the inlay core member comprises a shape chosen from a rhomboid or trapezoid;
   a post assembly comprising the inlay core and the post member, wherein the bottom end of the inlay core is axially attached to the coronal end of the post member;
   wherein the post assembly has a second coronal end and an apical end; wherein the post assembly is configured to fits the margins of the drilled canal;
   a veneer in close proximity to the top end of the inlay core, wherein the veneer has an enamel body-facing side, a top edge, and a labial-side; wherein the veneer has an average depth of about 0.2 mm to about 0.3 mm; wherein the top edge and the labial-side of the veneer is configured to be flush with an indentation on the labial and incisal side of an enamel body of an anterior tooth treated for root canal; wherein the veneer is buttressed on the lingual side, when placed on the enamel body with the post assembly; wherein the veneer is further configured to be positioned on the incisal side of the enamel body comprising a wrap-around of about 0.2 mm en for covering the incisal side.

* * * * *